(12) United States Patent
Briest

(10) Patent No.: US 8,114,428 B2
(45) Date of Patent: Feb. 14, 2012

(54) METHODS FOR MANUFACTURING A COMPOSITION FOR TREATING BONE AND/OR CARTILAGE DEFECTS

(75) Inventor: Arne Briest, Karlsruhe (DE)

(73) Assignee: SBF Synthetic Bone Factory GmbH (DE)

( * ) Notice: Subject to any disclaimer, the term of this patent is extended or adjusted under 35 U.S.C. 154(b) by 71 days.

(21) Appl. No.: 12/554,940

(22) Filed: Sep. 7, 2009

(65) Prior Publication Data

US 2010/0028404 A1 Feb. 4, 2010

Related U.S. Application Data

(63) Continuation of application No. PCT/IB2008/002367, filed on Sep. 5, 2008.

(60) Provisional application No. 60/993,146, filed on Sep. 10, 2007.

(30) Foreign Application Priority Data

Mar. 8, 2007 (DE) .......................... 10 2007 012 276

(51) Int. Cl.
| | |
|---|---|
| *A61K 38/00* | (2006.01) |
| *A61K 38/16* | (2006.01) |
| *A61K 38/17* | (2006.01) |
| *A61K 38/18* | (2006.01) |
| *A61K 38/30* | (2006.01) |
| *A61K 38/39* | (2006.01) |

(52) U.S. Cl. ........ 424/422; 424/423; 424/426; 424/484; 514/1.1; 514/7.6; 514/8.1; 514/8.2; 514/8.5; 514/8.8; 514/8.9; 514/17.2

(58) Field of Classification Search .......................... None
See application file for complete search history.

(56) References Cited

U.S. PATENT DOCUMENTS

| 4,619,989 A | 10/1986 | Urist |
|---|---|---|
| 5,141,905 A | 8/1992 | Rosen et al. |
| 5,366,875 A | 11/1994 | Wozney et al. |
| 5,631,142 A | 5/1997 | Wang et al. |
| 5,707,962 A | 1/1998 | Chen et al. |
| 5,932,207 A | 8/1999 | Schmidt |
| 5,958,441 A | 9/1999 | Oppermann et al. |
| 6,180,606 B1 | 1/2001 | Chen et al. |
| 6,306,424 B1 * | 10/2001 | Vyakarnam et al. .......... 424/426 |
| 6,551,995 B1 | 4/2003 | Oppermann et al. |
| 2002/0142391 A1 * | 10/2002 | Kivirikko et al. ............ 435/69.1 |
| 2004/0018595 A1 | 1/2004 | Rudolph et al. |
| 2007/0026437 A1 | 2/2007 | Wang et al. |

FOREIGN PATENT DOCUMENTS

| DE | 102004036881 A1 | 2/2006 |
|---|---|---|
| WO | WO9106324 A1 | 5/1991 |
| WO | WO9218142 A1 | 10/1992 |
| WO | WO9320857 A1 | 10/1993 |
| WO | WO02051449 A2 | 7/2002 |
| WO | WO2005033272 A2 | 4/2005 |

OTHER PUBLICATIONS

Bentz et al. (1998, J. Biomed. Mater. Sci. 39:539-548).*
Patel et al. (2006, The Spine Journal 6:397-404).*
PCT/ISA/210, IB, A3, Apr. 9, 2009, Briest.
Li et al. 2005 Spine 30: 890-896.
Morgenstern et al. 1998 Bioinformatics 14: 290-294.
Notredame et al. 1994 Nucl Acids Res 24: 1515-1524.
Roberge et al. 1995 Science 269: 202-204.
Tatusova et al. 1999 FEMS Microbiol Lett 174: 247-250.
Thompson et al. 1994 Nucl Acids Res 22: 4673-4680.

* cited by examiner

*Primary Examiner* — Elizabeth C Kemmerer
(74) *Attorney, Agent, or Firm* — Lawson & Weitzen, LLP; Sonia K. Guterman

(57) ABSTRACT

The present invention relates to compositions devices and methods for treating bone and/or cartilage defects, and a method for manufacturing such a composition or device. In a certain embodiment, the invention provides a device and/or composition for treating bone and/or cartilage defects, having at least one collagen, for example of animal origin, and further containing at least one substance having an osteo-inductive or chondro-inductive activity, at least one differentiation and/or growth factor having osteo-stimulative and/or chondro-stimulative effect, and at least one filling material, in which the composition is in the form of a lyophil.

20 Claims, No Drawings

METHODS FOR MANUFACTURING A COMPOSITION FOR TREATING BONE AND/OR CARTILAGE DEFECTS

RELATED APPLICATIONS

The present application claims the benefit of PCT applications PCT/IB08/002367 filed Sep. 5, 2008 in the International Bureau of WIPO, and PCT/EP08/001604 filed Feb. 29, 2008 in the PCT Receiving Office of the European Patent Office, and of U.S. provisional application 60/993,146 filed Sep. 10, 2007 in the U.S. Patent and Trademark Office, and German patent application DE 10 2007 012 276.6 filed Mar. 8, 2007, each of which is hereby incorporated by reference herein in its entirety.

TECHNICAL FIELD

The present invention provides compositions, devices, and method of manufacturing thereof; and methods for treating bone and/or cartilage defects.

BACKGROUND

Natural bone is made up of a combination of inorganic elements, organic elements, and water. Inorganic elements, for example hydroxyapatite, make up approximately 70% of natural bone. Organic elements such as collagen type I make up approximately 20% of natural bone, and water makes up approximately 10%. Bone-forming cells, for example osteoblasts, produce and secrete or bind the organic elements. Further, non-collagen proteins, in particular osteocalcin, osteonectin, osteopontin, cytokine, growth inducing factor, proteoglycan and fat are present in natural bone.

Natural bone is constantly being degraded and regenerated, i.e. re-modelled. Osteogenesis, i.e., bone regeneration, originates from the bone itself, as observed for example during healing of bone fractures. Thus, natural bone has the capability to generate new functional bone.

In many cases, however, regeneration of natural bone is restricted. This may be caused by, for example, the extent of a bone defect or by different functional disorders, for example metabolic disturbances. Treatment of bone defects remains an important field, for example in orthopedics, repair to jaws, teeth and hands, surgery in connection with accidents, and facial surgery.

Bone defects have different origins, caused for example by cysts, atrophies, or tumors. Complicated comminute fractures, congenital deformities and loosening of implants also cause bone defects. There is increasing focus on the reconstruction of bone defects using suitable materials.

Bone graft substitute products on the market include InFuse® manufactured by Medtronic Sofamor Danek (Minneapolis, Minn.), and OP-1® Putty manufactured by Stryker Corporation (Kalamazoo, Mich.). These products are sold as kits that separately contain a bovine collagen scaffold and human recombinant Bone Morphogenic Protein ("rhBMP") in a vial.

InFuse® uses rhBMP-2 which prior to implantation is soaked onto a sponge. OP-1® Putty is provided as two components: a vial containing one gram dry powder of bovine collagen, OP-1®, rhBMP-7, aid another vial containing a putty additive of carboxymethylcellulose dry powder. Both components must be combined with saline to produce the implant. According to the OP-1® Putty package insert, 96% of patients treated with OP-1® Putty develop an immune response to the product.

With each of these products, the rhBMP component is applied to the scaffold is performed during the surgical procedure. Applying the rhBMP solution to the surface of the scaffold potentially results in a heterogeneous distribution of the rhBMP, i.e., certain areas of the scaffold will have a higher concentration of rhBMP than other areas of the scaffold. Further, as the surgeon is required to assemble the product in the operating room, there exists a risk of infection and inconsistent dosage from procedure to procedure.

There is a need for sterile homogeneous devices and compositions with high osteo-inductive or chondro-inductive activities and methods for treating bone and/or cartilage defects.

SUMMARY

The invention in one embodiment provides a composition for treating bone and/or cartilage defects, having at least one collagen, preferably of animal origin, and preferably containing at least one substance having an osteo-inductive or chondro-inductive activity, at least one differentiation and/or growth factor having osteo-stimulative and/or chondro-stimulative effect, and at least one filling material, in which the composition is in the form of a lyophil. In general, the at least one differentiation or growth factor is a protein or peptide, preferably a glycoprotein or glycopeptide, preferably a cytokine, for example the differentiation or growth factor is a human differentiation or growth factor. In a related embodiment, the differentiation or growth factor is recombinantly produced. In general, the differentiation or growth factor comprises at least one member of the TGF (Transforming Growth Factor) family. For example, the differentiation or growth factor comprises at least one member of the group of BMP (Bone Morphogenetic Proteins), preferably BMP-2 and/or BMP-7.

Alternatively, the differentiation or growth factor is a TGF-β (Transforming Growth Factor beta) or is a VEGF (Vascular Endothelial Growth Factor).

The composition in certain embodiments includes, the differentiation or growth factor in relation to the amount of collagen, osteo-inductive or chondro-inductive activity, as a share of about 0.005 to about 5 percent by weight, preferably from about 0.01 to about 4 percent by weight. For example, the differentiation or growth factor comprises a share of about 0.05 to about 2 percent by weight, preferably from about 0.1 to about 5 percent by weight, preferably firm about 0.5 to about 3 percent by weight. The composition further includes at least one scaffold material, preferably a scaffold material having osteo-conductive properties. For example, the scaffold is collagen, preferably type I collagen. Alternatively, or in addition the scaffold material is at least one selected from the group of ceramics, biologically compatible metals and biologically compatible polymers. Alternatively, or in addition the scaffold material is an extract of native bone, preferably a demineralized bone matrix (DBM). Alternatively the composition includes a growth factor having chondro-inductive properties, such as TFG-β.

In certain embodiments, the composition further includes at least one additional active substance, preferably at least one cytostatic and/or at least one antibiotic. For example the composition includes further at least one component selected from the group of: at least one recruiting factor, at least one adhesion factor, at least one growth factor and at least one maturation factor for osteogenesis or chondrogenesis.

In general, the collagen is of mammalian origin, preferably of human, bovine, porcine or equine origin. In general, the composition further includes pores, preferably interconnecting pores, preferably pores having a diameter in the range of about 100 μm to about 300 μm, and the composition has a sponge-like consistency. The pores can arise from a lyophilization process, from a tunneling of ice crystal across a thermal gradient, or from a granulation process. In general, the composition is at least partially bioresorbable, preferably completely bio-resorbable. The composition is produced in the form of a paste a gel or a lyophil. Accordingly, the composition has a substantially form-stable body.

In another embodiment, the invention provides a composition for treating bone and/or cartilage defects having at least one recombinant collagen, preferably of human origin, and preferably containing at least one substance having an osteo-inductive or chondro-inductive activity, such that the osteo-inductive or chondro-inductive activity is at least one recombinant bone morphogenesis protein (BMP). In general, the BMP is of mammalian origin, preferably of equine, porcine or bovine origin. For example, the BMP is of human origin. Similarly, the BMP has an amino acid sequence at least about 70% identical to a BMP of human origin. The BMP in certain embodiments is recombinantly produced in a yeast or in a bacterium. For example, the BMP is recombinantly produced in bacterium *Escherichia coli*, or in *Bacillus subtilis*, or *Streptomyces* spp. Alternatively, the BMP is recombinantly produced in a cell capable of protein glycosylation. For example, the BMP is produced in a cell selected from the group consisting of mammalian, bird, yeast, and insect.

In certain embodiments, the BMP, in relation to the amount of collagen comprises a proportion of about 0.005 to about 5 weight percent, preferably from 0.01 to 4 weight percent. The BMP comprises a proportion of about 0.05 to about 20 weight percent, preferably from about 0.1 to about 5 weight percent, preferably from 0.5 to 3 weight percent.

In certain embodiments, the further additionally includes at least one scaffold material having osteo-conductive properties. For example, the scaffold material includes collagen, preferably type I collagen, preferably human type I collagen. Alternatively the collagen is type III. The scaffold material comprises at least one substance selected from the group of tricalcium phosphate, ceramic materials, biologically compatible metals, and biologically compatible polymers. For example, the scaffold material is tricalcium phosphate or a biphasic material comprising tricalcium phosphate. These ceramics are made at different sintering temperatures as is well known to one of ordinary skill in the ceramics art. The composition can further include at least one additional active substance, preferably at least one cytostatic and/or at least one antibiotic. For example, the composition further includes at least one additional component having an activity selected from the group of at least one recruiting factor, at least one adhesion factor, at least one growth factor and at least one maturation factor for osteogenesis or chondrogenesis. In general the human collagen is recombinantly produced.

The composition in general has a porous form, with pores, preferably interconnecting pores, preferably with diameters having a size in the range of about 100 μm to about 300 μm such that the composition has a spongy consistency. The pores arise from the lyophilization or granulation process, as the composition is "non-woven" material.

The composition in general is substantially bioresorbable or is essentially completely bioresorbable. The composition is provided as a lyophil, a gel, or a paste, and is a substantially form-stable body.

Thus, an embodiment of the invention provides a composition for treating bone and/or cartilage defects comprising an aseptically prepared admixture of a recombinant human collagen and a recombinant human bone morphogenesis protein (BMP) such that the collagen and the BMP are sterile and are aseptically mixed and co-lyophilized or co-granulated. For example, the BMP has an amino acid sequence that is at least about 70%, about 80%, about 85%, about 90%, or at least about 95% identical to an amino acid sequence of a BMP of human origin. The BMP in certain embodiments is produced in a bacterium, for example, the BMP is produced in *E. coli*. Alternatively, the BMP is recombinantly produced in a cell capable of protein glycosylation. For example, the BMP is produced in a cell selected from the group consisting of a mammalian, bird, yeast, and insect cell. The BMP, in relation to the amount of collagen comprises a proportion of about 0.005 to about 5 weight percent, preferably from 0.01 to 4 weight percent. For example, the BMP comprises a proportion of about 0.05 to about 2 weight percent, preferably from about 0.1 to about 5 weight percent, preferably from about 0.5 to about 3 weight percent.

The invention in a further embodiment provides a method for manufacturing any of the above compositions, the method including: mixing components comprising at least one collagen, preferably of animal origin and preferably having at least one osteo-inductive or chondro-inductive activity, with at least one differentiation or growth factor having osteo-stimulative and/or chondro-stimulative activity, and co-lyophilizing the components to obtain an at least partly form-stable, spongy body. In an embodiment in which collagen is of non-human origin, the method further includes prior to mixing, contacting the collagen with a peptidase or protease, preferably trypsin. The method further involves, prior to mixing, concentrating the differentiation or growth factor, preferably in at least one separation step. A related embodiment of the method further includes prior to mixing, adding at least one scaffold material, such that the scaffold material has osteo-conductive properties and is selected from the group of ceramic materials, biologically compatible metals, biologically compatible polymers and extracts of native bone, preferably DBM, and mixing, preferably coating, with collagen; and mixing with at least one collagen, preferably of animal origin with an osteo-inductive or a chondro-inductive, active substance and/or at least one additive of at least one differentiation or growth factor with osteo-stimulative and/or chondro-stimulative effect; and colyophilizing the components to obtain an at least partly form stable, spongy body. The method according to the above is performed under aseptic conditions.

Also provided herein is use of at least one differentiation and/or growth factor with osteo-stimulative and/or chondro-stimulative effect, the use comprising mixing aseptically an aseptic or a sterile solution of the growth factor with an aseptic or a sterile solution of at least one collagen, preferably of animal origin and preferably having at least one osteo-inductive or chondro-inductive, active substance; and, co-lyophilizing aseptically the resulting mixture in a container for single use as an implant in surgery.

Further provided herein is use of at least one human bone morphogenesis protein (BMP) for treating a bone and/or cartilage defect during a surgical procedure, the use comprising adding the BMP to at least one human collagen and at least one scaffold material to obtain an admixture, and providing the admixture as an aseptic device for treating a bone and/or cartilage defect during a surgical procedure. The above uses are in the form of a device, which is provided as a surgery-ready unit dose. The composition is a lyophil, a gel or a paste.

Another embodiment herein provides a method for formulating a composition for treating bone and cartilage defects, the method comprising: mixing aseptically a solution of a recombinant human collagen with a solution of an amino acid sequence of a recombinant human bone morphogenesis protein; and granulating or lyophilizing aseptically the admixture to a gel, paste, or a lyophil having an at least partly form-stable shape and a spongy consistency. In general, the solution of the collagen and the solution of the bone morphogenesis protein have reduced microbial content includes, or are sterile. Thus the method includes, prior to the mixing, concentrating the collagen, preferably in at least one separation step, and the collagen is treated with acid or filter sterilized prior to or after concentrating. Further the method can include prior to mixing, providing at least one scaffold material selected from the group of ceramic materials, biologically compatible metals, biologically compatible polymers and extracts of native bone, preferably DBM; mixing or preferably coating the scaffold material with the collagen; and colyophilizing or co-granulating the admixture to obtain an at least partly form-stable, spongy body. Prior to mixing, the collagen is sterilized by filter sterilizing or acidifying, the scaffold material is irradiated, and mixing is performed under aseptic conditions.

Yet another embodiment of the invention herein provides a kit for treating a bone and/or cartilage defect during a surgical procedure, the kit having an aseptically prepared admixture in the form of a lyophil, a gel or a paste, the admixture comprising a recombinant human bone morphogenesis protein (BMP) and a recombinant human collagen, in a container. The kit is for example, such that the admixture is present in a surgery ready unit dose. In a related embodiment the kit further has instructions for direct use of the aseptic admixture as an implant without additional manipulation.

An embodiment of the invention herein provides an aseptic device for surgical implantation for treating bone and/or cartilage defects which has an admixture of a recombinantly produced human differentiation and/or growth factor having osteo-stimulative and/or chondro-stimulative effect and at least one scaffold material, such that the factor is at least about 70% identical in amino acid sequence to a human growth factor, and the device is provided as a single component for surgical implantation. In one embodiment, the growth factor is glycosylated. Alternatively, the growth factor is recombinantly produced in a cell of a yeast, a mammal or a bird. For example, the growth factor is non-glycosylated, the growth factor is recombinantly produced in a bacterium, for example, in *E. coli*.

In general the growth factor in the device is a member of the TGF (Transforming Growth Factor) family. For example, the growth factor is at least one of Bone Morphogenetic Proteins (BMP) comprising BMP-2, BMP-7, BMP-9, BMP-16; Vascular Endothelial Growth Factor (VEGF); Transforming Growth Factor β (TGFβ), Platelet Derived Growth Factor (PDGF), Insulin-like Growth Factor (IGF) and p15. In one particular embodiment, the growth factor is a human BMP-2 or a human BMP-7 that is recombinantly produced and is nature identical. In general, the embodiments of the device that include collagen, the ratio of the differentiation or growth factor in relation to the amount of collagen comprises a share of about 0.005 to about 5 percent by weight, preferably from about 0.01 to about 4 percent by weight. For example, the growth factor comprises a share of about 0.05 to about 2 percent by weight, preferably from about 0.1 to about 5 percent by weight, preferably from about 0.5 to about 3 percent by weight.

The device in related embodiments includes at least one scaffold material, preferably a scaffold material having an osteo-conductive activity. For example, the scaffold is collagen having an amino acid sequence substantially identical to a human collagen. Further, the collagen is recombinantly produced. Alternatively or in addiction, the scaffold material is at least one selected from the group of ceramics, biologically compatible metals and biologically compatible polymers. The device can further include at least one additional active substance selected from the group of at least one cytostatic agent and/or at least one antibiotic. Alternatively, the device can further include at least one component selected from the group of: a recruiting factor, an adhesion factor, a growth factor and a maturation factor for osteogenesis or chondrogenesis. The device in general is a co-lyophil or a co-granulate and is a spongy form-stable body that comprises pores. The pores have a diameter in the range of about 100 μm to about 300 μm, and such that the admixture has a consistency and stable form of a surgical sponge. The device admixture in related embodiments is at least partially bio-resorbable, and is preferably completely bio-resorbable. The admixture is generally aseptically prepared from aseptic or sterile components. The device in various embodiments is provided in a closed container. In a particular embodiment, the admixture is aseptically lyophilized in the container. For example, the container is aseptically covered with a material capable of unidirectional passage of solvent molecules during lyophililization.

In general the scaffold material includes human recombinant collagen. For example, the collagen is selected from at least one of a type I collagen and a type III collagen. Alternatively or in addition, the scaffold material comprises a mineral. For example, the mineral is selected from the group consisting of: tricalcium phosphate, ceramic materials, biologically compatible metals, and biologically compatible polymers. In certain embodiments, the device includes collagen that is cross-linked using a commonly known reagent for cross-linking proteins. For example, the collagen is covalently internally cross-linked to itself, or the collagen is covalently linked to the growth factor. Thus the collagen is covalently cross-linked in solution to the growth factor to obtain a matrix, and then the matrix is lyophilized aseptically and used as an implant in a subject for treatment of a bone and/or a cartilage defect.

Accordingly, following implant into the subject, the matrix is subsequently metabolized releasing slowly the covalently bound growth factor such as BMP-2 or BMP-7, compared to release of an otherwise identically constituted and non-covalently bound matrix releasing growth factor in a burst at an early time point following implant into the subject. In certain embodiments of the device, the covalently cross linked collagen is obtained by contacting the collagen and osteo- and/or chondro-stimulating factors with a bidentate, low molecular cross-linking reagent selected from the group of commonly used in protein and peptide chemistry reagents: 1-ethyl-3-(3-dimethylaminopropyl)-carbodiimide (EDC), succinic anhydride, a di-isocyanates, an activated and properly protected amino acids, a double activated polyethylene-glycol, and an activated carbon hydrate to obtain quantitative binding of the reagent to the collagen. Accordingly, the device, following quantitative binding of the reagent to collagen is further prepared by the steps of: removing excess reagent by dialyzing, to obtain a modified collagen that retains protein features having a biological activity selected from the group of osteoinductive, chondro-inductive, osteo-conductive and chrondo-conductive; mixing the modified collagen with the factor/s for a time appropriate for cross-linking; and lyophilyzing, such that the steps are performed aseptically. The device in embodiments above includes materials that are aseptic, such that the device has a reduced microbial content.

In yet another embodiment, the device contains at least one additional component that retards release of the growth factor from the scaffold, for example from the collagen. The additional component retards release of the growth factor by non-covalent affinity, for example, the additional component is a plasma protein such as fibrin or a globulin. The additional component is in related embodiments of human origin, and/or is recombinantly produced.

DETAILED DESCRIPTION

A problem in treatment of bone and cartilage defects is that certain synthetic materials currently used to repair bone defects are poorly absorbed or are non-bioresorbable. These include ceramic materials, for example porous calcium phosphate ceramics. Such materials have useful osteo-conductive properties, i.e., the materials are able to provide regenerating bone tissue with a structure creating matrix (guide structure) with sufficient mechanical stability. Bone generating cells bind to materials with osteo-conductive properties, and then precipitate a bone matrix around or inside this material. Ceramic materials, however, remain in an unchanged state in the body, and are consequently overgrown and penetrated by the newly generated bone.

Bioresorbable bone replacement materials include synthetic polymers such as polylactide and polyglycolide. Such synthetic materials are degraded in vivo, usually by hydrolysis. Degradation of these materials can lead to a release of acidic by-products such as lactic acid or glycolic acid, causing undesired local hyper-acidification in the body.

Bone replacement materials currently used to repair bone defects include extracts of natural bone, such as bovine bone, porcine bone, or equine bone. Demineralized bone is a natural bone material in which the inorganic portion (mineral portion) has been removed and the remaining organic matrix substantially retains the natural endogenous collagen with other additional proteins. The extract retains a portion of the functional properties of the original bone. Further, these extracts of bone are found to enhance repair of bone defects.

Bone replacement materials and methods of manufacturing thereof, are shown in for example WO 91/06324 A1 and WO 93/20857 A1, and are commercially available products COLLOSS® and COLLOSS® F, which are collagen extracts of bovine bone and equine (E) bone respectively. These products contain collagen type I of animal origin in combination with endogenous growth and differentiation factors retained and bound to the collagen.

COLLOSS® and COLLOSS® E are provided in the form of a lyophilized extract. These products show osteo-conductive and osteo-inductive activity, and have a further differentiating activity when contacted to stem cells. The term, "osteo-inductivity" as used herein means that the substance or material initiates regeneration of bone (osteogenesis) and stimulates regeneration of bone (osteo-stimulation), and thus promotes bone growth. The regeneration activity has been demonstrated in vivo, and also in cell culture ex vivo. Under certain circumstances, materials having these properties can be manipulated to amplify the regeneration process compared to normal bone growth. The osteo-conductive effects of each of the above products, however, are not sufficient for certain applications.

Similar considerations apply to cartilage defects and to remedies for cartilage defects. The term, "chondro-inductivity" as used herein means that the substance or material initiates regeneration of cartilage (chondrogenesis) and stimulates regeneration of cartilage (chondro-stimulation), and thus promotes cartilage growth.

A complex for growth of bone tissue that includes a bone derived component, a bone derived chemotactic component, a bone derived adhesion component, and a bone derived growth factor is shown in WO 91/06324 A1 (corresponding to U.S. Pat. No. 5,932,207 issued Aug. 3, 1999) which is herein incorporated by reference in its entirety. This patent shows examples of the adhesion component, fibronectin, tenascin, cytotactin, laminin, chondroinectin, collagen yes IV, V, VII, N-CAM, L-CAM, and integrin, however without a filling agent that increases the osteo-conductive effect as well as an osteo-inductive effect of the complex.

Osteogenic compositions are shown in Chen et al. (U.S. Pat. Nos. 5,707,962, issued Jan. 13, 1998, and 6,180,606, issued Jan. 30, 2001). Osteogenic devices are shown in Opperman et al. (U.S. Pat. Nos. 5,958,441, issued Sep. 28, 1999, and 6,551,995, issued Apr. 22, 2003).

The compositions and devices provided herein contain a structural component having osteo-inductive and/or osteo-conductive properties, such as collagen, for example a collagen of animal origin. The animal origin of the collagen contained in the composition and device provided herein is not limiting. In certain embodiments of the device and composition herein, the collagen of the composition is of human origin, and contains at least one osteo-inductive or chondro-inductive active substance of human origin. In alternative embodiments, the collagen is of nonhuman animal origin, for example of bovine, porcine or equine origin.

The devices and compositions further include at least one additive of at least one differentiation and/or growth factor, having osteo-stimulative and/or chondro-stimulative activity. These differentiation and/or growth factors are, for example, proteins or peptides, such as cytokines, glycoproteins or glycopeptides.

In certain embodiments, the differentiation and/or growth factors are primarily human differentiation or growth factors and are combined with human collagen. In alternative embodiments, the human differentiation or growth factor is combined in the device with a collagen of xenogenic origin (in relation to human), i.e., of non-human animal origin, for example, bovine, porcine or equine origin.

In general, the differentiation or growth factor of human or animal origin is recombinantly produced. The term "recombinant" refers to proteins produced by manipulation of genetically modified organisms, for example micro-organisms.

In accordance with the present invention, polynucleotide sequences that encode differentiation or growth factors are used in recombinant DNA molecules to direct the expression of the differentiation or growth factors in appropriate host cells. To express a biologically active human differentiation or growth factor, a nucleotide sequence encoding the differentiation or growth factor, or functional equivalent, is inserted into an appropriate expression vector, i.e., a vector that contains the necessary nucleic acid encoding elements that regulate transcription and translation of the inserted coding sequence.

Methods that are well known to those skilled in the art are used to construct expression vectors containing a sequence encoding the differentiation or growth factor and appropriate transcriptional or translational controls. These methods include in vitro recombinant DNA techniques, synthetic techniques and in vivo recombination or genetic recombination. Introduction of deletions, additions, or substitutions is achieved using any known technique in the art e.g., using PCR based mutagenesis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989.

A variety of expression vector/host systems are utilized to contain and express a human differentiation or growth factor encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. Alternatively, chemical methods are used to synthesize the differentiation or growth factor amino acid sequence, whole or in part. For example, peptide synthesis can be performed using various solid-phase techniques (Roberge et al., Science 269:202, 1995) and automated synthesis may be achieved, for example, using the 431A peptide synthesizer (available from Applied Biosystems of Foster City, Calif.) in accordance with the instructions provided by the manufacturer.

The differentiation or growth factor in another embodiment is at least one member of the TGF (Transforming Growth Factor) family. TGF family growth factors include, for example, various cytokines such as members of the TGF-β family, that include the BMP family (Bone Morphogenetic Proteins), for example, BMP-2 and BMP-7. In certain embodiments, the differentiation and/or growth factor is BMP granulated with for example polylactide (micro capsules).

BMP compositions of human origin and of bovine origin, and processes of isolating BMP compositions and factors are shown in Urist (U.S. Pat. No. 4,619,989, issued Oct. 28, 1986).

For BMP-2, the nucleic acid sequence, amino acid sequence, structure, and composition of BMP-2, and methods of manufacture are shown in Wang et al. (U.S. Pat. No. 5,631, 142, issued May 20, 1997). Purified BMP-2 and BMP-4 proteins and processes for producing them are shown in Wang et al. (U.S. patent application number 2007/0026437, published Feb. 1, 2007). Methods of production of recombinant BMP-2 are shown in Rainer et al. (U.S. patent application number 20040018595, published Jan. 29, 2004).

Recombinant human BMP-2 is also commercially available from Shenandoah Biotechnology, Inc. (Warwick, Pa.).

Purified BMP-7 proteins and processes for producing them are shown in Wozney et al. (U.S. Pat. No. 5,366,875, issued Nov. 22, 1994). DNA sequences encoding BMP-7 proteins are shown in Rosen et al. (U.S. Pat. No. 5,141,905, issued Aug. 25, 1992). Recombinant human BMP-7 is also commercially available from Shenandoah Biotechnology, Inc. (Warwick, Pa.).

Each of the above references is incorporated by reference in its entirety.

Additional suitable differentiation or growth factors that are used in compositions and devices herein include VEGF (Vascular Endothelial Growth Factor), IGF1 (Insulin Growth Factor 1), FGF (Fibroblast Growth Factor) and PDGF (Platelet Derived Growth Factor). Alternatively, a functional fragment of any of the above mentioned differentiation or growth factor is used. The term "functional fragment" refers to molecules of a modified structure and/or sequence that provide the same biological function as the above mentioned differentiation or growth factors. Functional fragments include proteins that contain naturally occurring or engineered alterations, including any of a deletion, an addition, a substitution or other modification. A functional fragment is exemplified by a protein having a naturally occurring sequence for a region of any of the above mentioned differentiation or growth factors by a corresponding region of a growth factor from another mammalian species, including but not limited to, bovine, canine, feline, caprine, ovine, porcine, murine, and equine species.

The term "substantially identical" is used herein to refer to a first amino acid sequence that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60%, or 65% identity, preferably at least 75% identity, more preferably at least 85%, 90%, 91%, 92%, 93%, 94%, 95%, 96%, 97%, 98%, or 99% identity.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences are accomplished using a mathematical algorithm. Percent identity between two amino acid sequences is determined using an alignment software program using the default parameters. Suitable programs include, for example, CLUSTAL W by Thompson et al., Nuc. Acids Research 22:4673, 1994 (www.ebi.ac.uk/clustalw), BL2SEQ by Tatusova and Madden, FEMS Microbiol. Lett. 174:247, 1999 (www.nobi.nlm.nih.gov/blast/bl2seq/bl2. html), SAGA by Notredame and Higgins, Nuc. Acids Research 24:1515, 1996 (igs-server.cnrs-mrs.fr/~cnotred), and DIALIGN by Morgenstern et al., Bioinformatics 14:290, 1998 (bibiserv.techfak.uni-bielefeld.de/dialign).

In certain embodiments, the device or composition provided herein is engineered to provide for slow time-release of the active agents. For example, the device or composition further includes at least one additional component capable of retarding release of the differentiation or growth factor from the composition. Retarding release components are, for example a "sticky" protein capable of substantial nonspecific binding, such as a protamine and a plasma protein such as globulin, albumin, and fibrin. Protamine is an alkaline protein extracted from fish sperm and has a molecular weight of about 5000 Daltons. In an alternative embodiment for retarding release, the growth or differentiation factor is covalently bound to the collagen, for example by a protein cross-linking agent.

In certain embodiments of the invention provided herein, the device or composition further includes at least one filler or filling material. The filling or filler material has several purposes, such as providing the composition with additional mechanical stability and/or stability of form or shape. In general, the filling material has osteo-conductive properties, and provides additional surfaces for cell proliferation and/or cell differentiation.

The devices or compositions that contain filling materials such as collagen and at least one osteo-inductive or chondro-inductive active substance are manufactured to specific quantities of each component in the composition. Relative to the amount of collagen, the osteo-inductive or chondro-inductive active substance is contained in an amount of about 0.005 to about 5.0 mass percent, for example about 0.01 to about 4.0 mass percent. In other embodiments, the additive is contained in an amount of about 0.05 to about 2.0 mass percent, for example about 0.1 to about 5.0 mass percent or about 0.5 to about 3.0 mass percent.

The filling material is typically collagen, such as type I collagen. The collagen is obtained from skin, tendon, and/or from bone tissue. In certain embodiments, the collagen is of non-human origin, and the tendon is animal tendon, such as equine tendon. In alternative embodiments, the collagen is a recombinantly produced collagen, for example, recombinantly produced human collagen. Further, non-collagen filling materials are within the scope of the compositions and devices herein. Such filling materials are usually contained in the devices herein in the same amounts and proportions as the collagen relative to the osteo-inductive or chondro-inductive active substance.

Additional filling materials suitable to the compositions and devices herein include ceramic materials, biologically compatible metals, and biologically compatible polymers. Ceramic materials include tricalciumphosphate (TCP), hydroxyapatite (HA), calcium sulfate, CMC (carboxylmethyl cellulose), sepharose, polyarylate, and mixtures of such materials. In certain embodiments, the filling material is a β-tricalciumphosphate. Such filling materials are, present in the compositions and devices herein in relation to the total volume of the remaining elements, at least about 50 volume percent, at least about 80 volume percent, at least about 95 volume percent, or at least about 99 volume percent.

Ceramic filling materials are useful because the ionogenic elements of such materials, i.e., the fixed group of atoms in an ion exchanger that are either ionized or capable thereof, constitute the main elements of natural bone and mineral bone substance, and are therefore suitable bio-mimetic materials.

Ceramic material is used as a filling material in the commercially available product OSSAPLAST® (commercially available from Ossacur, Stuttgart, Germany). This product includes a bioresorbable and granulated β-tricalciumphosphate with a high interconnecting porosity and a large specific surface.

Filling material is further exemplified by a biologically compatible metal. Examples of biologically compatible metals are magnesium, titanium and tantalum. Further, magnesium is also bioresorbable. Examples of biologically compatible polymers include synthetic polymers such as polylactide and polyglycolide. The filler agent in other embodiments is a derivative of native bone, for example, demineralized bone matrix (DBM).

In certain embodiments, the filler agent provides additional osteo-inductive or chondro-inductive activity to the composition and/or device herein. These filler materials include leukotrienes, cytotactin, tenascin, laminin, fibronectin and cytokines such as BMP-1, BMP-2, BMP-7, IGF-1, TGF-β1, FGF and PDGF.

In embodiments of methods of manufacture of the devices and compositions, the filler material is added to a collagen matrix by modifying the collagen prior to the addition. For example, the collagen is chemically modified so that the filling material is covalently cross-linked to the collagen. In an alternative embodiment, the filling material is added prior to preparation of the collagen matrix, or is a naturally occurring factor in the corresponding collagen matrix, i.e., the collagen and the filling material are combined by the process by which they are provided, for example, the growth factor is extracted from its biological source, viz., natural bone. In this embodiment, the osteo-inductive or chondro-inductive filling materials are present in a native form in association with the collagen.

One or more additional agents that provide a further desired biological effect with respect to treating bone or cartilage defects is added in other embodiments of the devices and compositions provided herein. Such additional agents are, for example, a cytostatic agent or an antibiotic, or a combination thereof.

In another embodiment, the device or composition further includes recruiting factors, for example a chemotactic agent (such as a chemotaxin or a leucotriene). The recruiting factor induces an infiltration of the composition into cells of a human, such as mesenchymal stem cells, cartilage premonitory stem cells, fibroblasts and/or thrombocytes. Alternatively these substances are added to the collagen, or are supplemented.

In another embodiment, the collagen contained in the composition further includes at least one adhesion factor, for example cytotactin, tenascin, laminin and/or fibronectin. These substances function to fix recruited or migrant cells in the composition or device according to the invention at its application location (implant location).

In certain embodiments, the above mentioned factors are naturally found in collagen, such that the filling material can be purified, or can be obtained in a complex that is a mixture of a plurality of these factors. The collagen component of the composition or device can include a substantial portion of the osteo-inductive properties of the filling materials that are involved in vivo for regeneration of bone and/or cartilage. A set of the naturally occurring filling materials mentioned above can have overlapping or redundant active functions, such that a partial or substantial loss of activity of one or more active substances may be compensated by the presence of other active substances in the composition.

Collagen of animal origin is commercially available in isolation form, e.g., COLLOSS® (bovine) and COLLOSS® E (equine) from Ossacur (Oberstenfeld, Germany). These products contain native active substances, so that the combination of the collagen and active substance provides a native, functional unit, the composition corresponding in a particular manner to the in vivo milieu, in which bone and/or cartilage regeneration is induced.

Methods of extracting collagen from natural bone are well known in the art. Collagen is extracted from natural bone by the following exemplary procedure: pulverizing natural bone; degreasing by extraction with an organic solvent; demineralizing with acid treatment, for example hydrochloric acid; incubating with chelating agents, for example ethylenediamine tetraacetic acid (EDTA) or 2-amino-2-hydroxymethyl-1,3-propanediol (TRIS) or a combination thereof; and extracting with guanidine, for example guanidine hydrochloride; followed by purifying the extract; and physically forming the extract into a configuration suitable for implanting. One of ordinary skill in the art of biology will understand that one or more of the above steps may be omitted as necessary or additional steps are within exemplary procedures.

In certain embodiments, the composition or device is in a porous configuration or form. In other embodiments, the device or composition has a substantially spongy consistency. The type filling material, as described above such as, ceramic materials, e.g., tricalciumphosphate (TCP), determines the extent of porosity of the composition or device.

In certain embodiments, the porosity is an interconnecting porosity, i.e., the pore structure is located between the individual particles of the filling material, and within the particles. A porous device or composition is advantageous for cell infiltration from cells of the subject recipient of the implant into the pores of the device or composition, for example bone and/or cartilage cells, or progenitor cells thereof.

Pores of the composition or device or the pores of the filling material, respectively, have diameters of at least about 100 µm, particularly diameters of about 100 µm to about 300 µm. In certain embodiments, the pores of the composition or device or the pores of the filling material, respectively are about 200 µm in diameter.

In certain embodiments, the composition and device according to the invention is at least partly bio-resorbable. In a related embodiment, the composition and device according to the invention is completely bioresorbable. Following implantation, the implant to treat the bone or cartilage defect is completely replaced by new bone or new cartilage.

In another embodiment, the composition according to the invention is a lyophil, for example colyophil. The advantages of a lyophil are described in the Examples below.

In another embodiment, the composition according to the invention is a substantially form-stable body, for example, a porous spongy structure with sufficient mechanical stability to withstand mechanical manipulation involved with implantation. Such a composition includes osteo-inductive/chondro-inductive properties for regeneration of bone or cartilage.

In general, the composition and/or device provided herein is produced in an aseptic or sterile procedure and is packed in a sterile procedure. Further, the device is unitary and requires no manipulation so it can be implanted directly for the treatment of the bone or cartilage defect without additional preparation.

Another aspect of the present invention provides a new method for manufacturing the above described composition according to the invention. The method involves providing a collagen, for example a collagen of human origin, recombinant collagen, or a collagen of animal origin, which includes at least one osteo-inductive or chondro-inductive active substance; mixing this collagen with an additive of at least one differentiation or growth factor with osteo-stimulative and/or chondro-stimulative effect and possibly other substances; and colyophilizing these components to form an at least partially stable spongy body.

In certain embodiments of the method according to the invention, prior to mixing the collagen with the at least one additive, the collagen is treated with at least one peptidase, for example an endopeptidase such as trypsin. Treating with an endopeptidase removes undesired proteins or peptides, for example telopeptides that are found in the collagen (with or without active substance), are removed from this collagen fraction. In general, the endopeptidase used in the described treatment, such as trypsin, is provided in such an amount that it is depleted or completely removed before affecting the osteo-conductive activity of the collagen fraction. One of ordinary skill in the art of biochemistry determines appropriate concentrations of the endopeptidase and duration of treatment to the mixture that does not affect the activity of the collagen fraction. In other embodiments, collagen, for example type I collagen, is not digested by an endopeptidase.

In other embodiments of the method, the collagen is concentrated prior to mixing the collagen with the additional one or more compounds. Concentrating the collagen prior to mixing the collagen with additional components is beneficial under certain circumstances with respect to properties of the resulting colyophilized spongy body. Concentrating the collagen fraction with added osteo-inductive or chondro-inductive active substances provides that the concentration of the active substances in the total device having the collagen fraction together with the active substances of the additive, is great enough to substantially provide a sufficient concentration of the active substances within the total volume of the composition, for example, the spongy body.

Concentrating a mixture having endogenous or added osteo-inductive or chondro-inductive active substances is accomplished by methods well known to one of ordinary skill in the art in biology. For example, concentrating involves at least one centrifuging step, at least one separation step through a suitable membrane, and/or at least one precipitation step by means of gravity. An exemplary concentration of a protein-containing suspension of the product COLLOSS® E with a dry substance content (TS) of 1.5 mg protein/g to 2.0 mg protein/g suspension. The above described methods result in an increased TS content between 2.0 mg protein/g to 20.0 mg protein/g suspension.

In general, a resulting spongy body provides the user with a homogeneous distribution of the biologically active substances that form the spongy body. In general, the filling materials constitute a larger volume of the spongy body than the biological materials. The biological materials obtained from collagen and from added agents such as differentiation or growth factors only cover the volume between the particles of the filling materials.

In certain embodiments, collagen is mixed with a porous filling material with osteo-conductive properties, as described above. An exemplary process for obtaining collagen with osteo-conductive properties involves mixing collagen and an above mentioned filling material with osteo-conductive properties. During this mixing, the collagen is applied as a coating on the inner and outer surfaces of the porous filling material with osteo-conductive properties. Further steps include lyophilizing the resulting mixture to obtain collagen with osteo-conductive properties, i.e., collagen having an osteo-inductive/osteo-stimulative or chondro-inductive/chondro-stimulative effect. The method further provides at least one collagen with osteo-inductive or chondro-inductive, active substance and/or an additive of at least one differentiation or growth factor with osteo-stimulative and/or chondro-stimulative effect. The resulting mix is finally colyophilized to form a substantially stable spongy body.

In general, the method described above is performed under aseptic conditions, yielding a resulting device or composition according to the invention that is in aseptic or even sterile. In alternative embodiments, a variety of sterilization methods are used to obtain the composition that is aseptic or is sterile. In one embodiment, prior to use in the method according to the invention, each individual component of the composition according to the invention is sterilized, for example, filtered under sterile conditions to remove bacteria and viruses. In another embodiment, the method further includes packaging the composition or device in a sterile manner to provide an aseptic composition or device or a sterile composition or device.

The characteristics of the composition according to the invention shown herein are explicitly made characteristics of the method according to the invention and the use according to the invention, respectively.

In the devices provided herein, presence of at least one differentiation and/or growth factor with osteo-stimulative and/or chondro-stimulative effect with at least one collagen results in several advantages, as shown below. Each of the agents induces and also amplifies the osteogenic or chondrogenic properties of the device of the present invention. Further, presence of growth factor with the collagen results in amplification of already existing form stability of the composition. The composition herein is optimized by interaction between the osteo-inductive and osteo-conductive effect provided by the growth factor, and the form stability/supporting function provided by the filling material. In another embodiment, any reduction of osteo-inductive effect of the composition resulting from addition of filling materials that are not osteo-inductive is compensated or overcome by relatively small increases in the amount of the additive to the composition.

Further, colyophilization in the production process, produces a finalized composition, i.e., the components of the composition are already mixed to form a ready-to-use device. Another embodiment provides a ready-to-use device that is convenient for use, for example by a surgeon. Because the composition is produced in a sterile manner, it can be taken directly from a sterile package and used during surgery to repair a bone or cartilage defect.

COLLOSS® E is available in the form of an aqueous suspension, which is concentrated by performing at least one separation step. The suspension obtained from the concentration is then mixed with further additives and elements of the composition. After obtaining a homogenous mixture, the elements of this mixture are colyophilised. A porous, spongy, stable body occurs.

To obtain a sterile or aseptic device, the entirety of the steps in the production process are performed under aseptic conditions, and the individual components of the composition are filtered in a sterile manner in advance of their use in the manufacturing process.

Example 2

Compositions of the Invention

Compositions according to the invention are prepared from the following elements:

| No. | Collagen matrix | Additive | Further additives |
|---|---|---|---|
| 1 | 5 mg COLLOSS E | 0.01 mg human BMP-2 (or BMP-7) | — |
| 2 | 5 mg COLLOSS E | 2 mg human BMP-2 (or BMP-7) | — |
| 3 | 100 mg COLLOSS E | 0.01 mg human BMP-2 (or BMP-7) | — |
| 4 | 100 mg COLLOSS E | 2 mg human BMP-2 (or BMP-7) | — |
| 5 | No. 1-No. 4 | No. 1-No. 4 | 1 ml TCP* (OSSAPLAST) |
| 6 | No. 1-No. 4 | No. 1-No. 4 | 1 ml TCP (OSSAPLAST) 5 mg collagen type I |
| 7 | No. 1-No. 4 | No. 1-No. 4 | 1 ml TCP (OSSAPLAST) 100 mg collagen type I |
| 8 | — | 0.01 mg human BMP-2 (or BMP-7) | 1 ml TCP (OSSAPLAST) 5-100 mg collagen type I |
| 9 | — | 2 mg human BMP-2 (or BMP-7) | 1 ml TCP (OSSAPLAST) 5-100 mg collagen type I |

*Tricalcium phosphate

The invention having now been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications cited throughout this application, are hereby incorporated by reference.

EXAMPLES

Example 1

Production of Compositions According to the Invention

The following method is used for production of the compositions according to the invention.

The product COLLOSS® E, a collagen extract of equine bone tissue, is commercially available as described above. Methods of making this product are also described above and are shown in WO 93/20857 A1, which is herein incorporated by reference in its entirety. See also Spine 30:890-895, 2005. This material contains an active substance complex of naturally bound factors in a matrix of type I collagen.

Further examples of agents that, in certain embodiments are present in the devices and compositions of the invention include: BMP colyophilized with collagen and/or ceramic; BMP bound with a spacer (globulin, polyethylene glycol (PEG), albumin, protamine, and fibrin) to the collagen; and a suspension of collagen with a protamine, a globulin, a fibrin, an albumin, and BMP and the suspension is then lyophilized.

The BMP-2 or BMP-7 or other growth factors in the device or composition are for example a recombinantly produced human protein. The collagen type I used is for example a recombinant human collagen. Use of recombinant human BMP-2 or BMP-7 and recombinant human collagen is advantageous when administering these compositions to human beings because of severe antigenic activity of xenobiotic proteins.

What is claimed is:
1. A method for aseptically manufacturing a mammalian recombinant collagen composition, the method comprising:
  contacting the collagen with a peptidase or protease, wherein the mammalian collagen is of non-human origin and has at least one of an osteo-inductive activity or a chondro-inductive activity, and is filter sterilized;
  adding at least one scaffold material, wherein the scaffold material has osteo-conductive properties and is selected from the group of ceramic materials, biologically com- patible metals, biologically compatible polymers and extracts of native bone, and mixing with the collagen;

adding at least one differentiation or growth factor having osteo-stimulative and/or chondro-stimulative activity and the scaffold; and, co-lyophilizing the components to obtain an at least partly form-stable, spongy body, wherein the method is performed under aseptic conditions, thereby aseptically manufacturing the composition.

2. A method for formulating a composition for treating bone and cartilage defects, the method comprising:

concentrating a solution of recombinant human collagen, wherein the collagen is treated with acid, and is filter sterilized;

mixing aseptically the recombinant human collagen with a solution of a recombinant human bone morphogenesis protein (BMP), wherein the collagen and bone morphogenesis protein are sterile or have a reduced microbial content; and granulating or co-lyophilizing aseptically the admixture to a gel, paste or a lyophil having an at least partly form-stable shape and a spongy consistency.

3. The method according to claim 2, further comprising prior to mixing, providing at least one scaffold material selected from the group of ceramic materials, biologically compatible metals, biologically compatible polymers and extracts of native bone; mixing the scaffold material with the collagen, wherein the scaffold material is irradiated prior to mixing with the collagen; and co-lyophilizing or co-granulating the admixture to obtain an at least partly form-stable, spongy body.

4. The method according to claim 1, wherein the differentiation or growth factor having osteo-stimulative and/or chondro-stimulative activity is at least about 70% identical in amino acid sequence to a human growth factor, wherein the growth factor is at least one selected from the group of a Bone Morphogenesis Protein (BMP); a Vascular Endothelial Growth Factor (VEGF); a Transforming Growth Factor β(TGFβ); a Platelet Derived Growth Factor (PDGF); and Insulin-like Growth Factor (IGF); and a p15.

5. The method according to claim 1, further comprising after contacting the collagen with peptidase or protease, aseptically filtering the collagen.

6. The method according to claim 2, wherein the recombinant human bone morphogenesis protein (BMP) in relation to the amount of collagen comprises a proportion in weight percent in a range selected from the group of: about 0.005 to about 5, about 0.01 to about 4, about 0.05 to about 2, about 0.1 to about 5, and about 0.5 to about 3.

7. The method according to claim 2, further comprising after mixing covalently linking the collagen to the bone morphogenesis protein aseptically with a protein cross-linking the reagent selected from the group consisting of: 1-ethyl-3-(3-dimethlyaminopropyl)-carbodiimide (EDC), succinic anhydride, di-isocyanates, activated and protected amino acid, double activated polyethylene-glycol, and activated carbon hydrate.

8. The method according to claim 7, further comprising after cross-linking: removing the excess cross-linking reagent by dialyzing to obtain a modified collagen that retains a biological activity selected from the group of osteo-inductive, chondro-inductive, osteo-conductive and chondro-conductive.

9. The method according to claim 2, further comprising prior to co-lyophilizing, adding at least one agent selected from the group of: an anti-microbial agent, a cytostatic agent, an anti-inflammatory agent, and a vitamin.

10. The method according to claim 2, further comprising prior to co-lyophilizing, adding at least one additional active substance selected from the group of: a cytokine, a recruiting factor, an adhesion factor, a growth factor, and a maturation factor for osteogenesis or chondrogenesis.

11. The method according to claim 2 further comprising prior to co-lyophilizing, adding at least one agent for retarding release of the growth factor from the scaffold.

12. The method according to claim 11, wherein the agent for retarding release is a plasma protein.

13. The method according to claim 2, further comprising after concentrating the recombinant human collagen, mixing the collagen with the BMP and at least one additional differentiation and/or growth factor having osteo-stimulative and/or chondro-stimulative effect, wherein the additional differentiation or the growth factor having osteo-stimulative and/or chondro-stimulative activity is at least about 70% identical in amino acid sequence to a human growth factor, wherein the growth factor is at least one selected from the group of Vascular Endothelial Growth Factor (VEGF), Transforming Growth Factor β (TGFβ), Platelet Derived Growth Factor (PDGF), Insulin-like Growth Factor (IGF) and p15.

14. The method according to claim 13, wherein the additional differentiation or growth factor in relation to the amount of collagen comprises a percent share by weight percent in a range selected from: about 0.005 to about 5; about 0.01 to about 4; about 0.05 to about 2; about 0.1 to about 5; and about 0.5 to about 3.

15. The method according to claim 13, further comprising covalently linking the collagen to the BMP and the additional growth factor aseptically.

16. The method according to claim 1, wherein the native bone comprises demineralized bone matrix (DBM).

17. The method according to claim 1, wherein mixing the scaffold with the collagen further comprises coating the scaffold with collagen.

18. The method according to claim 3, wherein the native bone comprises demineralized bone matrix (DBM).

19. The method according to claim 3, wherein mixing the scaffold with the collagen further comprises coating the scaffold with collagen.

20. The method according to claim 12, wherein the plasma protein comprises fibrin.

* * * * *